US006881417B1

(12) United States Patent
Laughlin

(10) Patent No.: US 6,881,417 B1
(45) Date of Patent: *Apr. 19, 2005

(54) METHOD, APPARATUS, AND COMPOSITION FOR AUTOMATICALLY COATING THE HUMAN BODY WITH PLURAL COMPONENTS

(75) Inventor: Thomas J. Laughlin, Grapevine, TX (US)

(73) Assignee: Laughlin Products, Inc., Grapevine, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/664,572

(22) Filed: Sep. 17, 2003

Related U.S. Application Data

(63) Continuation of application No. 10/191,708, filed on Jul. 8, 2002, now Pat. No. 6,656,455, which is a continuation of application No. 09/677,184, filed on Oct. 2, 2000, now Pat. No. 6,416,747, which is a continuation-in-part of application No. 09/664,218, filed on Sep. 18, 2000, now Pat. No. 6,251,374, which is a continuation-in-part of application No. 09/294,689, filed on Apr. 19, 1999, now Pat. No. 6,199,557, which is a continuation-in-part of application No. 08/946,764, filed on Oct. 8, 1997, now Pat. No. 5,922,333.

(60) Provisional application No. 60/157,547, filed on Oct. 4, 1999, and provisional application No. 60/154,948, filed on Sep. 21, 1999.

(51) Int. Cl.[7] .......................... A61K 7/00; A61K 7/42; A61K 7/44; A61K 31/74
(52) U.S. Cl. .......................... 424/401; 424/59; 424/60; 424/78.02; 424/78.03; 424/78.06; 424/400
(58) Field of Search .................. 424/59, 60, 78.02, 424/78.03, 78.06, 400, 401

(56) References Cited

U.S. PATENT DOCUMENTS

| 870,766 A | 11/1907 | Eaton |
| 1,262,638 A | 4/1918 | Class |
| 1,982,509 A | 11/1934 | Frank .......................... 128/1 |
| 2,700,384 A | 1/1955 | Ivory .......................... 128/204 |
| 2,949,403 A | 8/1960 | Andreadis et al. ............. 167/90 |
| 3,060,097 A | 10/1962 | Fellows ........................ 167/91 |
| 3,177,120 A | 4/1965 | Black et al. .................. 167/90 |
| 3,272,713 A | 9/1966 | Runge .......................... 167/90 |
| 3,856,934 A | 12/1974 | Kligman ...................... 424/62 |
| 3,868,950 A | 3/1975 | Kato ............................ 128/66 |
| 3,920,808 A | 11/1975 | Fusaro ......................... 424/59 |
| 3,932,151 A | 1/1976 | Lau ............................. 55/229 |

(Continued)

FOREIGN PATENT DOCUMENTS

| BE | 814319 | 8/1974 | |
| DE | 141293 | 9/1901 | |
| DE | 36 05 807 | 2/1986 | |
| DE | G 93 19 158.8 | 12/1993 | |
| EP | 0 712 625 | 5/1996 | ............ A61K/7/42 |
| FR | 2725362 | 10/1994 | |
| WO | WO 94/12146 | 6/1994 | |
| WO | WO 00/54892 | 9/2000 | ............ B05B/15/12 |

OTHER PUBLICATIONS

Color Additives: Dihydroxyaceton, Federal Register, 38: No. 148, p. 20615, Aug. 2, 1973.

Dihydroxyaceton–containing sunless or self–tanning lotions, Stanley B. Levy, Journal of the American Academy of Dermatology, 27: No. 6, pp. 989–993, 1992.

Formulating Effective Self–Tanners with DHA, T. Kurz, Cosmetics and Toiletries, 109: No. 11, pp. 55–60, 1994.

Non–Carcinogenicity of Dihydroxyaceton by Skin Painting, Frank J. Akin and Edward Marlowe, Journal of Environmenta Pathology and Toxicology, 5: No. 5, pp. 349–351, 1984.

Persistence of Skin Color and Fluorescence after Treatment with Dihydroxyaceton, J.A. Johnson & R.M. Fusaro, Dermatology 188: p. 247, 1994.

Spray Application Processes, Binks Training Division, TD49–2R–4, Aug. 1995.

Theory & Practice of Artifical Tanning Literature & Patent Survey, E. Futterer, Cosmetics and perfumes, 88: No. 8, pp. 31–33, 1973.

Fusaro et al. (1966), Sunlight protection in normal skin, *Archives of Dermatology*, vol. 93, pp. 106–111 (Jan. 1966).

Fusaro et al. (1970), Erythropoietic protoporphyria IV. Protection from sunlight. *Br. Med. J.*, vol. 1, pp. 730–731.

Fusaro et al. (1972). Protection against light sensitivity with dihydroxyacetone/naphthoquinone. *Int. J. Dermato*, vol. 11, pp. 67–70.

Fusaro et al. (1974). Photoprotection of patients sensitive to short and/or long ultraviolet light with dihydroxyacetone/naphthoquinone. *Dermatologica*, vol. 148, pp. 224–227.

Johnson et al. (1973). Protection against long ultraviolet light with dihydroxyacetone/naphthoquinone. *Dermatologica*, vol. 47, pp. 104–108.

Fusaro et al. (1971). Sunlight protection in patients with Chloropromazine light sensitivity. *Int. J. Dermato*, vol. 10, pp. 198–200.

Primary Examiner—Shelley A. Dodson
(74) Attorney, Agent, or Firm—Michael A. O'Neil

(57) ABSTRACT

In a system for coating human skin, a chemical composition, such as a cosmetic or medical formulation, is uniformly coated over the entire body or selected parts of the body of the person being coated. The system includes atomization of the coating composition, containment of the atomized spray, and residual recovery which together yield a novel method for applying chemical compositions. An improved self-tanning composition is useful in conjunction with the system is also disclosed. Also disclosed is a plural component self-tanning system.

6 Claims, 9 Drawing Sheets

U.S. PATENT DOCUMENTS

| | | | |
|---|---|---|---|
| 4,231,289 A | 11/1980 | Domicent | 98/115 |
| 4,453,914 A | 6/1984 | Huniu | 431/121 |
| 4,453,941 A | 6/1984 | Jacobs | 8/424 |
| 4,749,130 A | 6/1988 | Utzinger | 239/543 |
| 4,826,681 A | 5/1989 | Jacquet et al. | 424/613 |
| 4,832,943 A | 5/1989 | Grollier et al. | 424/59 |
| 4,874,412 A | 10/1989 | Nowack | 55/385.1 |
| 5,073,996 A | 12/1991 | Schinle | 4/601 |
| 5,089,269 A | 2/1992 | Noda et al. | 424/456 |
| 5,102,660 A | 4/1992 | Forestier et al. | 424/401 |
| 5,153,174 A | 10/1992 | Band et al. | 514/12 |
| 5,232,688 A | 8/1993 | Ziegler et al. | 424/59 |
| 5,268,166 A | 12/1993 | Barnett et al. | 424/47 |
| 5,273,214 A | 12/1993 | Huffstutler | 239/279 |
| 5,299,743 A | 4/1994 | Sieth et al. | 239/248 |
| 5,302,378 A | 4/1994 | Crotty et al. | 424/59 |
| 5,397,394 A | 3/1995 | Orr | 118/634 |
| 5,456,211 A | 10/1995 | Stevenson | 119/157 |
| 5,460,192 A | 10/1995 | McClain | 132/333 |
| 5,494,674 A | 2/1996 | Barnett et al. | 424/401 |
| 5,512,278 A | 4/1996 | Mundschenk | 424/78.06 |
| 5,545,399 A | 8/1996 | Lee et al. | 424/59 |
| 5,567,420 A | 10/1996 | McEleney et al. | 424/60 |
| 5,603,923 A | 2/1997 | Robinson et al. | 424/60 |
| 5,662,890 A | 9/1997 | Punto et al. | 424/59 |
| 5,664,593 A | 9/1997 | McClain | 132/333 |
| 5,700,452 A | 12/1997 | Deckner et al. | 424/59 |
| 5,773,014 A | 6/1998 | Perrier et al. | 424/401 |
| 5,880,314 A | 3/1999 | Shinomiya et al. | 568/729 |
| 5,922,333 A | 7/1999 | Laughlin | 424/401 |
| 6,117,118 A | 9/2000 | Laughlin et al. | 604/290 |
| 6,199,557 B1 | 3/2001 | Laughlin | 132/200 |
| 6,214,322 B1 | 4/2001 | Castro et al. | 424/59 |
| 6,231,837 B1 | 5/2001 | Stroud et al. | 424/59 |
| 6,298,862 B1 | 10/2001 | Laughlin | 132/200 |
| 6,305,384 B1 | 10/2001 | Laughlin | 132/200 |
| 6,416,747 B1 | 7/2002 | Laughlin | 424/59 |
| 6,421,180 B1 | 7/2002 | Montgomery et al. | 359/618 |
| 6,431,180 B1 | 8/2002 | Laughlin | 132/200 |
| 6,439,243 B1 | 8/2002 | Laughlin | 132/333 |
| 6,443,164 B1 | 9/2002 | Parker et al. | 132/333 |
| 6,446,635 B1 | 9/2002 | Laughlin | 132/200 |
| 6,468,508 B1 | 10/2002 | Laughlin | 424/59 |
| 6,474,343 B1 | 11/2002 | Laughlin | 132/200 |
| 6,554,208 B1 | 4/2003 | Venuto, Sr. | 239/207 |

SELECT COATING COMPOSITION

↓

ATOMIZE COMPOSITION

↓

CONTAIN ATOMIZED COMPOSITION

↓

DIRECT ATOMIZED COMPOSITION ONTO SKIN

↓

CAPTURE RESIDUAL COMPOSITION

METHOD, APPARATUS, AND COMPOSITION FOR AUTOMATICALLY COATING THE HUMAN BODY WITH PLURAL COMPONENTS

CROSS REFERENCE TO RELATED APPLICATIONS

This application is a continuation application of application Ser. No. 10/191,708 filed Jul. 8, 2002, now U.S. Pat. No. 6,656,455, which is a continuation of application Ser. No. 09/677,184 filed Oct. 2, 2000, now U.S. Pat. No. 6,416,747, which is continuation-in-part of application Ser. No. 09/664,218 filed Sep. 18, 2000, now U.S. Pat. No. 6,251,374, which is a continuation-in-part of application Ser. No. 09/294,689 filed Apr. 19, 1999, now U.S. Pat. No. 6,199,557, which is a continuation-in-part of application Ser. No. 08/946,764 filed Oct. 8, 1997, now U.S. Pat. No. 5,922,333.

CLAIM OF PRIORITY

Applicant claims priority based on provisional patent application Ser. No. 60/154,948 filed Sep. 21, 1999, and on provisional patent application Ser. No. 60/157,547 filed Oct. 4, 1999.

TECHNICAL FIELD

The present invention relates generally to systems for automatically coating the human body or selected parts thereof with predetermined fluids. More particularly, the invention relates to an automated self-tanning (a/k/a sunless tanning) system, and to an improved self-tanning composition.

BACKGROUND OF THE INVENTION

The application of various fluids to all or selected parts of the human body has been known literally for centuries. However, despite the long standing and widespread practice of coating the human body with various fluids, there has never been a successful way of automatically coating the human body. Therefore, prior to the present invention, it has been necessary to apply fluids to the body manually.

Manual application of fluids to the human body results in numerous disadvantages. First, it is almost impossible to uniformly coat the human body with fluids using manual application techniques. This is true even in the case of fluids that are provided in aerosol or spray form because such fluids must be rubbed in after application. Second, the application of fluids to certain parts of the human body, for example, the back, require the availability of an assistant in order that proper manual application can be attempted.

The foregoing difficulties are particularly apparent in the case of artificial tanning processes, hereinafter sometimes referred to as self-tanning or sunless tanning compositions and systems. Artificial tanning has been known for more than 40 years, with artificial tanning products appearing on the U.S. market as early as 1959. The two key types of tanning processes are by colorants and bronzers.

Tanning by colorants is based on the color reaction which occurs between components of the skin and the colorant. The most commonly used chemical for artificial tanning is dihydroxyacetone (DHA). It is widely used in commercial artificial tanning products, and is recognized as safe and effective by the U.S. Food and Drug Administration (FDA). DHA reacts solely with the stratum corneum. It interacts with amines, peptides and free amino acids to generate a Maillard reaction. The resulting products are cyclic and linear polymers that have a yellow or brown color.

Two common bronzers are juglone and lawsone. Both are naphthoquinones. When applied to skin, lawsone produces an orange hue and juglone produces a greenish-brown tan. They are sometimes used in combination with DHA to modify the color or hue of the tan or to intensify the color.

Numerous forms of artificial tanning products are now on the market. They include:
lotions,
creams,
gels,
oils,
sprays.

These products are mixtures of a chemically-active skin colorant or a bronzer with combinations of the following:
moisturizers,
preservatives,
anti-microbial,
thickeners,
solvents,
emulsifiers,
fragrances,
surfactants,
stabilizers,
sunscreens,
pH adjusters,
anti-caking agents,
ingredients to alter the color reaction.

Users of these products often experience significant problems associated with the current methods for applying artificial tanning formations to skin. These problems include the following.

If not properly dried, the formulation will streak or form blotches with time. The net result is a very nonuniform tan, with light or dark streaks or blotches.

Certain parts of the body will stain more intensely when the formulation is spread manually. This differential staining is due to enhanced absorption of certain skin tissue and the tendency of certain tissue to retain more absorb or trap more formulation (e.g., the wrinkles in the elbows and knees and the dense tissue in the palms).

Most products designed for manual application require components such as thickeners and polymers, which often inhibit the efficacy of DHA.

Current formulations typically take about 20 minutes to dry to the touch, and about 1 hour before not transferring from skin to textiles.

Application of artificial tanning products is additionally complicated by the tendency of these formulations to stain materials containing amine molecules, including certain fabrics, certain types of carpet, and certain wall coverings and paint.

In spite of all of these problems, artificial tanning is becoming increasingly popular. It is apparent that a need exists for a superior application system which solves the foregoing problems.

There is also a need for a superior applications system for many other applications, including but not limited to:
self-tanning formulations,
sunscreens,
suntan lotions,
tanning accelerators,
sunburn treatments,
insect repellants, skin toners,
skin bleaches,
skin lighteners,
anti-microbial compositions,
moisturizers,
exfoliants,
nutriments or vitamins,
massage aids,
muscle relaxants,
skin treatment agents,
burn treatment agents,
decontamination agents,
cosmetics,
wrinkle treatments or removers.

There are specific and significant problems with the manual coating of each of these products. The artificial tanning application provides a good illustration of the types of problems normally encountered when manually coating with these products. Artificial tanning is also one of the most demanding applications in that uniformity of the coating is critical to assure uniform tanning.

SUMMARY OF THE INVENTION

The present invention comprises a system for automatically coating the human body, including a method of and apparatus for uniformly and rapidly coating all or selected parts of the human body. The system includes apparatus which atomizes (also referred to as aerosolization, nebulization, mist generation, fog generation or spray generation) a chemical composition and deposits it uniformly over all or selected parts of the human body. It is not necessary for the individual receiving the treatment nor anyone else to manually apply any of the formulation. Also, a containment system is provided which restrains and collects residue from the application process. The system can optionally recycle the materials used.

There are several major advantages resulting from the use of the invention:

Uniform application minimizes or eliminates streaking,

No assistant is required for applying the composition,

The entire skin surface receives the same exposure to the composition, so the uniformity of the coating is greatly enhanced over manual application, The optimal formulation for atomization is very simple, and does not require the addition of components which may inhibit the efficacy of the applied material, The application time can be as quick as a few seconds, and complete drying can occur in just a few minutes, The containment system drastically reduces the unwanted environmental impact, Multiple applications can be used to better control the amount of material applied per unit area, and additional substances can be applied in separate applications.

The invention may be practiced utilizing a unitary construction including both a coating chamber and apparatus for coating a person situated within the coating chamber. A door provides ingress to and egress from the coating chamber which is provided with vertically disposed arrays of spray discharging nozzles situated at spaced apart points around the periphery of the chamber. A blower circulates air through the coating chamber to effect drying following the coating procedure and to aid in containment of excess spray. An air compressor supplies liquid for coating and compressed air for spraying the coating liquid to the nozzles situated within the coating chamber.

In accordance with another aspect of the invention, there is provided a plural component system for coating the human body. The plural component system may comprise a single discharge nozzle which simultaneously or sequentially receives fluid from separate sources. Alternatively, the plural component system may comprise two or more discharge nozzles each receiving fluid from a separate source. Both techniques keep various components of the composition to be applied to the skin entirely separate until the moment of application.

The present invention further comprises an improved self-tanning composition. The improved self-tanning composition is particularly adapted for use in conjunction with the method and apparatus hereof.

REFERENCES

U.S. Patent Documents

| | | | |
|---|---|---|---|
| 3,932,151 | 1/1976 | Lau | 55/229 |
| 4,231,289 | 11/1980 | Dornicent | 98/115 |
| 5,268,166 | 12/1993 | Barnett | 424/047 |

Foreign Patent Documents

WO 94/12146 June 1994 PCT Int'l Appl.

Other Publications

Akins, F. J. and Marlowe, E., "Non-Carcinogenicity of Dihydroxyacetone by Skin Painting," Journal of Environmental Pathology and Toxicology, 5: No. 5, pp. 349–351 (1984).

Federal Register, "Color Additive Dihydroxyacetone" 38: No. 148, p. 21615, 2 August 1973.

Futterer, E., "Theory and Practice of Artificial Tanning: Literature and Patent Survey," Cosmetics and Perfumes, 88: No. 8, pp. 31–33 (1973).

Johnson, J. A. and Fusaro, R. M., "Persistence of Skin Color and Fluorescence after Treatment with Dihydroxyacetone," Dermatology 188: pp. 247 (1994).

Kurz, T., "Formulating Effective Self-Tanners with DHA," Cosmetics and Toiletries, 109: No. 11, starting p. 55 (1994).

Levy, S. B., "Dihydroxyacetone-Containing Sunless or Self-tanning Lotions," Journal of the American Academy of Dermatology, 27: No. 6, pp. 989–993 (1992).

"Spray Application Processes," BINKS training brochure TD49-2R-4, August, 1995, BINKS Manufacturing Company, Franklin, Ill.

BRIEF DESCRIPTION OF THE DRAWINGS

A more complete understanding of the invention may be had by reference to the following Detailed Description when taken in conjunction with accompanied Drawings, wherein:

FIG. 1 is a flow chart illustrating the invention;

FIG. 2 is a diagrammatic illustration of the system for automatically coating the human body of the present invention comprising the minimum requirements thereof;

FIG. 3 is an illustration similar to FIG. 2 wherein the system of the present invention is further provided with containment apparatus;

FIG. 4 is an illustration similar to FIG. 3 wherein the system of the present invention is further provided with an air ventilation apparatus;

FIG. 5 is an illustration similar to FIG. 4 wherein the system of the present invention is further provided with collection apparatus for residual spray;

DETAILED DESCRIPTION OF THE INVENTION

Figure 3:
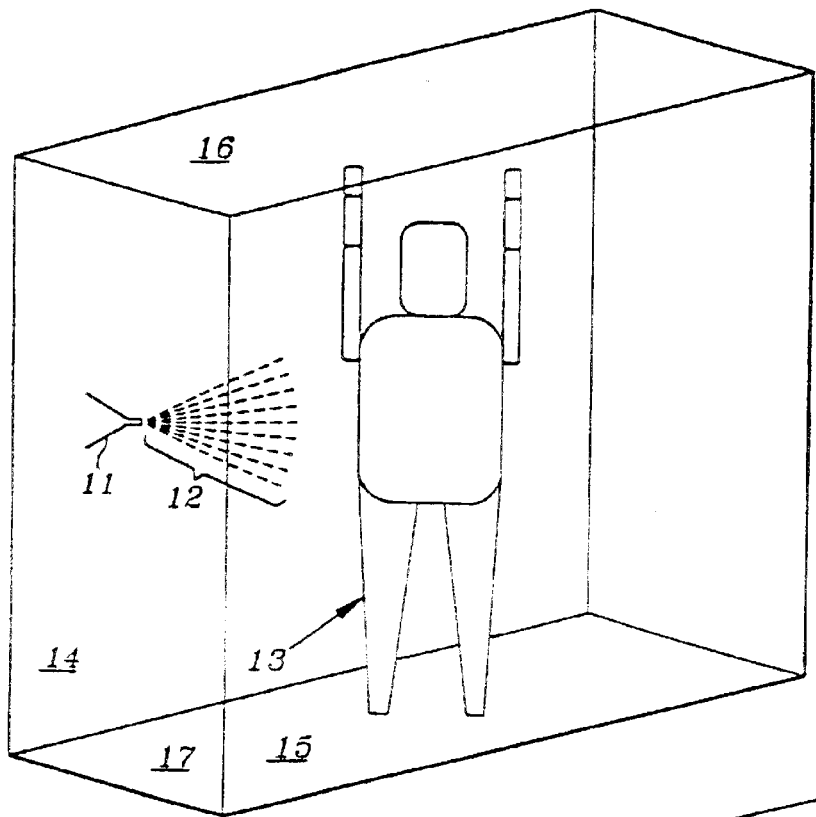

Referring now to the Drawings, and particularly to FIG. 1, the system for automatically coating the human body of the present invention may comprise an automated coating system for numerous types of formulations, including but not limited to the application of:

self-tanning formulations,
sunscreens,
suntan lotions,
tanning accelerators,
sunburn treatments,
insect repellants,
skin toners,
skin bleaches,
skin lighteners,
anti-microbial compositions,
moisturizers,
exfoliants,
nutriments or vitamins,
massage aids,
muscle relaxants,
skin treatment agents,
burn treatment agents,
decontamination agents,
cosmetics,
wrinkle treatments or removers.

The first component of such a system is the chemical composition. The suitability of a composition for coating is strongly influenced by its viscosity, with the preferred viscosity being close to that of water (1 centipoise). Compositions with viscosities in the 1 to 10 centipoise range generally atomize well, and viscosities in the 10 to 100 range can be atomized, but the resulting spray is not as fine. Higher viscosities can be atomized, and will work, but the spray is not as fine. Most currently marketed compositions of the aforementioned applications can be made suitable for atomization either as is or with appropriate dilution.

By way of example, a more detailed description of functional compositions for use in practice of the invention will be based on artificial tanning compositions. Six such compositions are given in Compositions 1, 2, 3, 4, 5, and 6. Individuals skilled in this art can create other compositions.

| Ingredient | % |
|---|---|
| COMPOSITION 1 | |
| Dihydroxyacetone | 3.0 |
| Water | 97.0 |
| COMPOSITION 2 | |
| Dihydroxyacetone | 3.0 |
| Denatured Ethanol | 20.0 |
| Water | 77.0 |
| COMPOSITION 3 | |
| Dihydroxyacetone | 12.0 |
| Denatured Ethanol | 20.0 |
| Water | 68.0 |
| COMPOSITION 4 | |
| Dihydroxyacetone | 10.0 |
| Commercial Sunless-Tanning Lotion | 15.0 |
| Water | 75.0 |
| COMPOSITION 5 | |
| Dihydroxyacetone | 9.0 |
| Commercial moisturizer | 20.0 |
| Citric acid | 0.3 |
| Commercial bath product | 0.6 |
| Bronzer | 6.0 |
| Water | 64.1 |

By way of example, a suitable commercial moisturizer would include Vaseline Brand Intensive Care Aloe and Naturals lotion (Chesebrough-Ponds, Greenwich, Conn.), and a suitable commercial bath product would include Vaseline Brand Intensive Care Foaming Creme Bath (Chesebrough-Ponds, Greenwich, Conn.). The bronzer is a combination of FD&C dyes that yield a golden brown color.

| COMPOSITION 6 | |
|---|---|
| Ingredient | % |
| Bronzer | 8.0 |
| Commercial moisturizer | 20.0 |
| Commercial bath product | 0.6 |
| Ethoxydiglycol | 2.0 |
| Water | 69.4 |

By way of example, a suitable commercial moisturizer would include Vaseline Brand Intensive Care Aloe and Naturals lotion (Chesebrough-Ponds, Greenwich, Conn.), and a suitable commercial bath product would include Vaseline Brand Intensive Care Foaming Creme Bath (Chesebrough-Ponds, Greenwich, Conn.). The bronzer is a combination of FD&C dyes that yield a golden brown color.

Foaming Creme Bath (Chesebrough-Ponds, Greenwich, Conn.). The bronzer is a combination of FD&C dyes that yield a golden brown color.

By way of example, suitable commercial sunless tanning preparations include Coppertone® Oil-Free Sunless Tanner (Schering-Plough, Memphis, Tenn.), Neutrogena® Glow Sunless Tanning Lotion for Face and Body (Neutrogena, Los Angeles, Calif.), and Kroger® Sunless Tanning Cream (Kroger, Cincinnati, Ohio).

Compositions 1, 2 and 3 are greatly simplified versions of the formulations now on the market or reported in the past. This simplification is possible due to the use of the present invention for applying compositions to skin. These simplified compositions have several advantages over more complex formulations, including:

faster drying, less potential inhibition of DHA efficacy, less potential for irritation from chemical components (because there are fewer components), less residue on the skin, less expensive, more environmentally friendly.

Compositions 4 and 5 illustrate how a commercial formulation not particularly well suited for atomization can be diluted, effectively atomized and uniformly coated on human skin. Similar dilutions of products representing the other aforementioned applications can be effectively atomized and coated on human skin.

There is no pH adjustment required for these compositions, although the pH can be adjusted to alter the hue of the resulting tan and to alter the dihydroxyacetone stability.

The optimal tanning occurs with DHA at a pH of below 6.0, preferably with the solution at a pH 3.0 to 4.0. Unbuffered DHA has a pH of about 5.5. The pH on the surface of human skin is also about 5.5. Nonetheless, these formulations can be used over a wide pH range, and buffers or pH adjusters can be added.

A preferred colorant is DHA. DHA is available from Rona (Hawthorne, N.Y.).

It is effective, safe, and approved by the FDA for this application. The preferred DHA concentration is 0.5% to 20%, with a more preferred range of 3% to 15%, and a most preferred range of 5% to 12%.

Numerous other colorants can also be used. Those agents include, but are not limited to:

crotonaldehyde pyruvaldehyde glycolaldehyde glutaraldehyde otho-phthaldehyde sorbose fructose erythrulose methylvinylketone food coloring Various dyes and UV blocking agents can be covalently linked to the colorant or can be mixed into the composition with the colorant.

Bronzers can also be used in combination with or as an alternative to DHA. Bronzers which can be used include, but are not limited to, lawsone and juglone. Combinations of DHA and bronzers can also be used, and can be used to modify the resulting color (hue) and intensity of the tan. The preferred range for lawsone, juglone, and FD&C dyes is 0.5% to 10.0% with the more preferred range of 1.0% to 5.0%.

Composition 6 is an example of a formulation containing only bronzers (no DHA). The preferred range of FD&C dyes in commercially formulated liquid form (e.g., food coloring by Adams Extract Co., Austin, Tex.) is 1 to 50%, with a more preferred range of 4 to 12%. Ethoxydiglycol is added to enhance the penetration of the dyes into the skin, to reduce transfer to clothing, and to assist in the stabilization of the formulation. The preferred ethoxydiglycol range is 1 to 20%, with a more preferred range of 2 to 10%.

Alcohol can be added to the composition to accelerate the rate of drying. Denatured ethanol (USP grade, commodity chemical) works well in this capacity. The preferred range for alcohol concentration is from 1.0% to 50.0%, with a more preferred range from 10.0% to 30.0%, and a most preferred concentration of 20.0%.

Other potential additives include:

moisturizers, preservatives, anti-microbials, thickeners, solvents, emulsifiers, fragrances, stabilizers, sunscreens, surfactants, pH adjusters, anti-caking agents, ingredients to alter the color reaction.

It typically requires about 100 ml of a 5.0% DHA composition to obtain a medium to dark tan over an entire adult body (about 2 square meters of skin). A single application of about 250 ml of a 9% dihydroxyacetone composition over an entire adult human body will result in a very dark tan. The exact amount of dihydroxyacetone required depends will result in a very dark tan. The exact amount of dihydroxyacetone required depends on the skin type and intensity of tan desired. The tan can last for about 2 to 7 days, but usually lasts for 3 to 4 days. Multiple applications will darken the tan.

The second component of the invention is the atomization of the composition. The required atomization can be obtained by a host of ways, most of which involve passing the composition through an orifice under pressure. Methods now used to atomize solutions include the use of the following systems:

- air atomization
    - siphon feed
    - gravity feed
    - pressure feed
        - internal atomization
        - external atomization
        - low pressure low volume
        - high volume low pressure
- airless atomization
    - pressurized through small orifices
    - air-assisted
    - air-assisted heated
    - electrostatic
        - using charged particles
        - heated charged particles
        - high speed rotational atomizers
- ultrasonic These forms of atomization are the basis for most methods of producing atomized sprays, including mis Using a single airless sprayer with a tip orifice of 0.6 mm, with a circular spray pattern of 12 inches at 12 inches from the tip, and with a flow rate of approximately 400 ml/min. the entire body (excluding the bottom of the feet) of an average-sized person can be coated with solution in 5 to 15 seconds. In practice, the underside of the feet usually gets slightly tanned also from exposure to small quantities of residual artificial tanning composition on the floor of the application area. The use of a single airless sprayer to apply a composition to human skin is illustrated in FIG. 2. In this figure and subsequent figures, 11 designates the orifice for atomization of the composition, 12 designates the atomized spray, and 13 designates the subject being sprayed. In this configuration, an operator must direct the flow of the spray. The configuration illustrated in FIG. 2 would also work for any of the other atomization methods aforementioned, and for any of the applications aforementioned. The preferred atomization method is the pressure-free air-atomization system, with an internal or external atomization configuration.

For a person to be coated as illustrated in FIG. 2 with an artificial tanning composition (or any composition of the applications aforementioned), several precautions should be taken. First, the person should hold their breath during the application and during the time required for the spray to clear. If this process is done in an open area, the coating should take about 5 to 15 seconds and the clearing of residues should take 1 to 10 seconds. Thus, the person would need to hold their breath for 6 to 25 seconds. Alternatively, they could wear a filter over their mouth, have a filter inside of their mouth, or use a breathing tube. They can also wear nose plugs or filters. Second, the eyes should be protected even though most of these formulations are not likely to injure the eye. The simplest and most effective protection is to keep the eyes closed. Goggles or patches also work well, although they leave uncoated areas that must be subsequently coated manually. Next, precautions need to be taken if one wants to avoid the exposure of scalp hair. Scalp hair can be protected with a shower cap or any other similar protective covering impervious to the coating compositions. Also, hair can be coated with a water insoluble material such as petroleum jelly. Similar protection can be used to protect hair on any other parts of the body. Next, if atomization is from a single source, it is recommended that the person being coated turn while being coated, or that the coating apparatus be moved around the person being coated, or there be a combination of these movements. Finally, care must be taken that the nozzle remain at least several inches from the person being coated to prevent any possible injection of composition into the person. Generally, spray injection occurs at pressures greater than 500 psi with the person actually contacting the atomization orifice. The pressures here are less than 80 psi, and more typically 10 to 40 psi, and the person being coated should be a foot or more from the orifice.

The issue of what to wear during coating is usually of great concern to the person being coated. In the case of coating with artificial tanning solution, the selection of what to wear is a matter of preference for the person being coated. The subject can be coated nude, with underwear, with a bikini or a bathing suit, or with some form of pasties covering their private parts.

The third component of the invention is containment of the spray. Containment is illustrated in FIG. 3. In this figure and subsequent figures, 14 and 15 designate side panels and 16 and 17 designate the top and bottom panels, respectively. This type of containment is similar to the containment of spray paint using paint booths in automobile refinishing. Alternatively, spray containment can be obtained using electrostatic forces, where the atomized spray is charged and the residual charged spray is removed by activating charged collection plates. Of course, precautions must be taken so that the person being sprayed and the operator are isolated from the charged plates.

Containment of the spray is very important for several reasons. These reasons include but are not limited to:
  reducing waste,
  avoiding spray getting onto and staining items in the immediate surroundings,
  facilitating capture and recovery processes,
  better control of air flow,
  better control of temperature and humidity.

This type of containment facilitates the use of this invention in enclosed areas such as stores or medical facilities.

Figure 4:
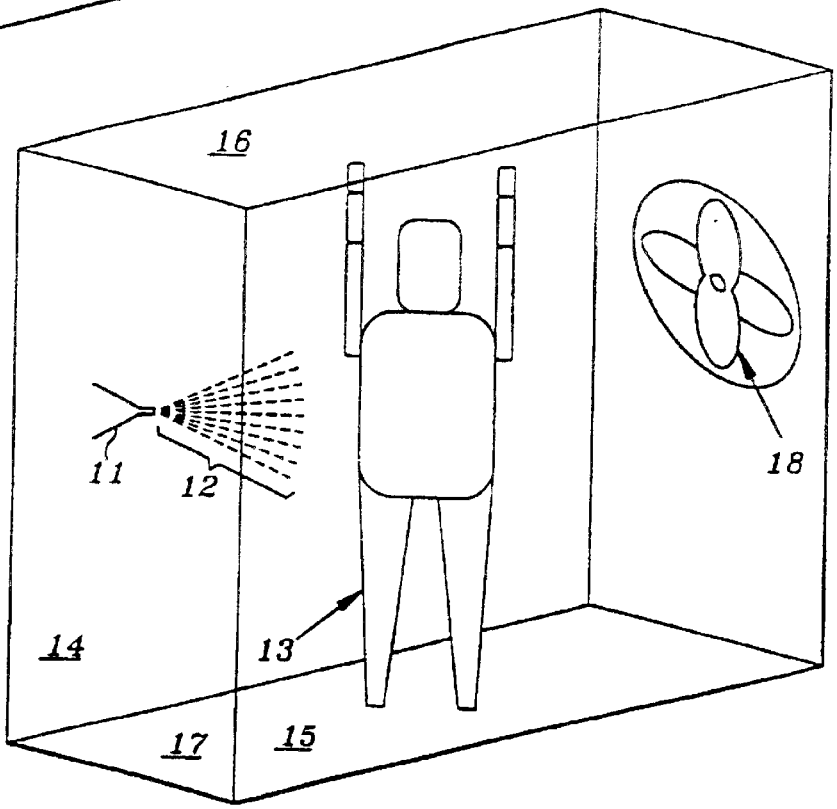

Control of air and spray flow is very important to the quality of the skin coating. It is highly preferable to have an exhaust fan drawing the spray towards the person being coated, and the residual composition out of the booth. In FIG. 4 is shown the addition of an exhaust fan 18. The fan offers several significant advantages to the invention. These advantages include but are not limited to:
  better control of air flow
  shorter exposure to residue spray, requiring less time to hold breath or breathe through filter or air line
  faster drying of the coated composition on skin
  better quality coating The fan 18 should have a flow of 10 to 5000 cubic feet per minute per square foot of opening, preferably 50 to 1000 cubic feet per minute per square foot, and most preferably 100 to 400 cubic feet per minute per square foot. At flow rates of below 100 cubic feet per minute per square foot, the air movement is sufficient to guide the cubic feet per minute per square foot, the air movement is sufficient to guide the atomized spray through the containment area. At flow rates of 100 to 400 cubic feet per minute per square foot, the atomized spray is being actively drawn through the containment area and the application and drying process is enhanced. At rates above 400 cubic feet per minute per square foot, the atomized spray is being accelerated and the exhaust flow plays a much more prominent role in the application process. The flow rate of the air through the containment area is therefore a major parameter which can be varied to modify the characteristics of the coating of the artificial tanning composition to the skin. The drying time for the composition deposited on skin is also affected by flow rate, with drying time decreasing as flow rates increase. At rates above 100 cubic feet per minute per square foot, the drying time (to the point of no transfer to other surfaces upon contact) is less than 5 minutes.

At any flow rate above 10 cubic feet per minute per square foot, the residual atomized spray is completely removed from the containment area within one second. This rapid removal is important to minimize the time the person being tanned is exposed to spray and has the potential to inhale this spray. In the absence of this air flow, the residual spray lingers in the area for several minutes, and traces can be detected hours later. This vigorous flow also protects any individuals or operators near the atomizing orifices from back spray.

The final element of this invention is recovery, or filtering, of residual composition.

Figure 5:
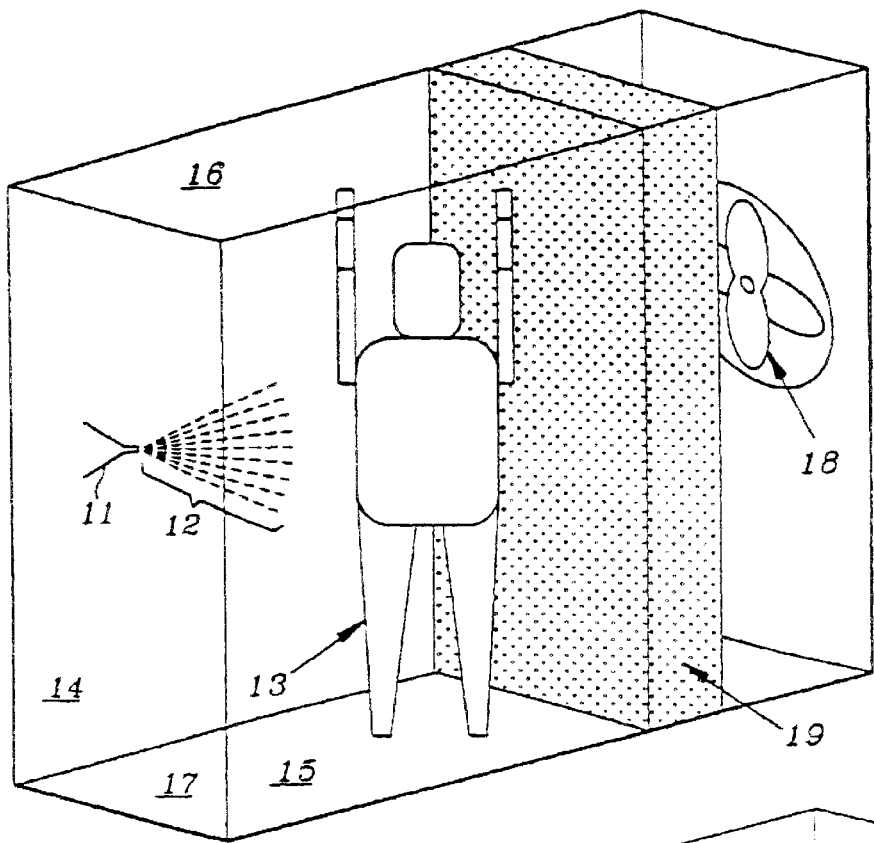

This feature greatly enhances the utility of the invention because it allows the system to be self-contained in an indoor environment and promotes a more environmentally friendly process. Without a recovery system, there is a potential for the exhausted residue to stain anything it contacts. Also, there could be an accumulation of residue with time. One configuration of the recovery system is shown in FIG. 5. In this figure and subsequent figures, the recovery system or filter is denoted as 19. Recovery of both particulates and solvents is possible. Potential filters include a high-efficiency filter such as Binks' (Franklin Park, Ill.) Paint Pockets or Columbus Industries' (Ashville, Ohio) High-Capacity Supra Mini-Mesh, a form of a carbon filter, a water-wash filter, or an exchange-type resin. The efficiency of particulate and solvent removal should be greater than 99%. As an alternative to high-efficiency filtering, the spray residuals could be vented to the outside environment.

Figure 6:
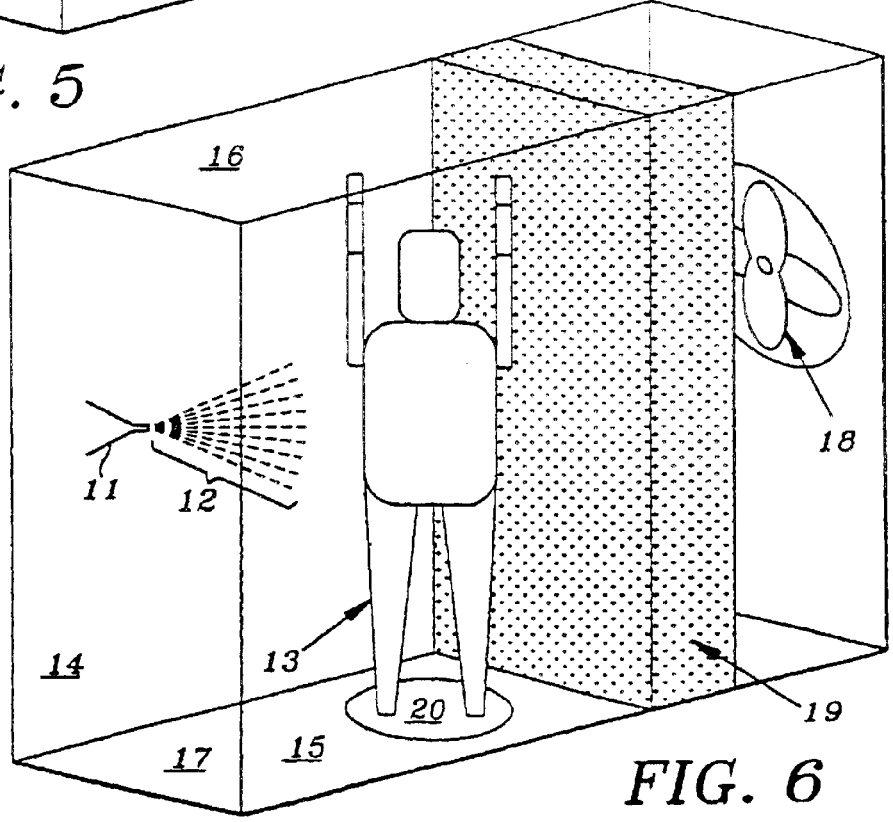
FIG. 6 is an illustration similar to FIG. 5 wherein the system of the present invention is further provided with apparatus to effect rotation of the human body being coated.
Figure 7:
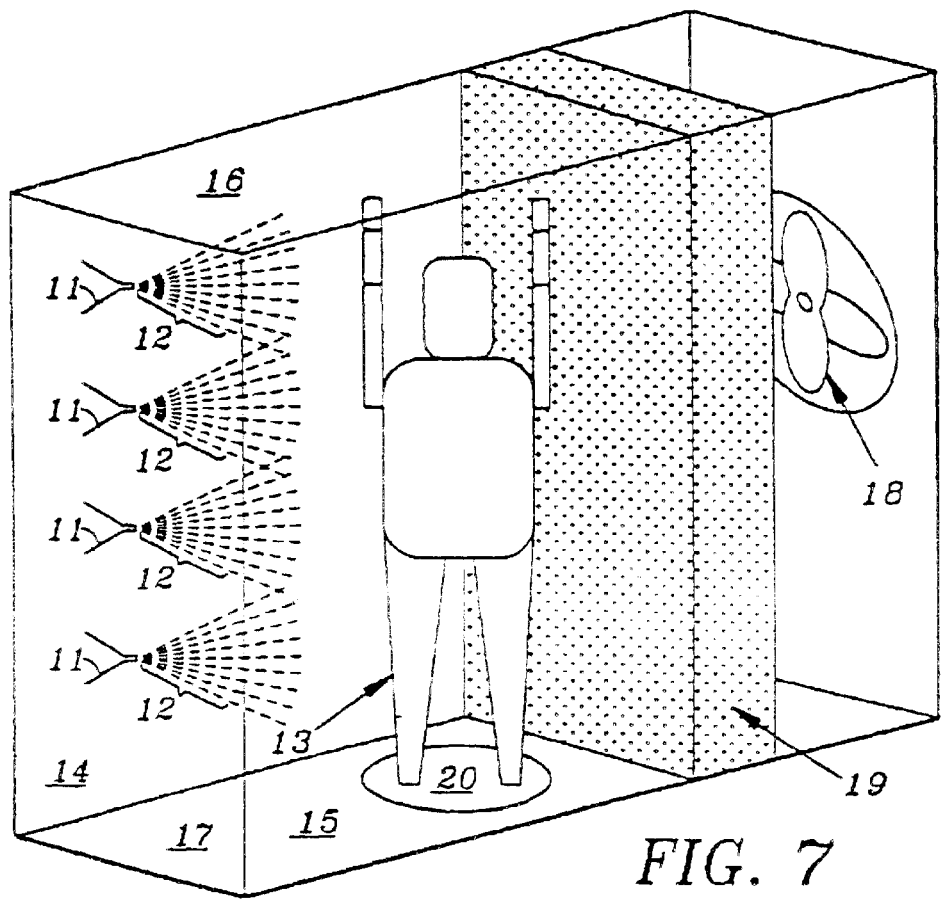
FIG. 7 is an illustration similar to FIG. 6 wherein the system of the present invention is further provided with multiple discharge nozzles.

Additional features adding to the utility of the invention are shown in FIG. 6 and FIG. 7. In FIG. 6 there is shown the addition of a motorized turntable 20. This turntable 20 will rotate the person being coated, eliminating rotation by the individual as a possible source of error or problems. It also is a major convenience for the person being coated. The preferred rate of rotation is in the range of 1 to 60 rpm, with a more preferred range of 5 to 20 rpm, with a most preferred rate of rotation of 12 rpm.

In FIG. 7 there is shown the use of multiple atomizing orifices. The use of multiple orifices facilitates the automation of this process, and reduces operator effort and potential error. It also reduces the time required to fully coat an individual. The typical round spray pattern is about 12 inches wide at 8 to 12 inches from the orifices, so a preferred spacing of multiple orifices will be 8 to 12 inches apart, but could be positioned from 1 to 48 inches apart. Fan patterns from wide-angle nozzles at 18 inches are typically 24 inches long and 9 inches wide. Using the preferred configuration, an individual can be coated in 5 seconds or less. In FIG. 7, the orifices are aligned in a vertical pattern. The coverage of more area at one time could also be obtained by rapidly moving one or more orifices along a track or by rapidly altering the angle of the orifice. Other patterns are possible, including combinations of vertical and horizontally aligned orifices. Orifices could also be aligned radially, with the subject being sprayed with orifices aligned from 0 to 360°. Another alignment is a horizontal ring containing orifices that surround the body. By vertically raising and lowering the horizontal ring, the entire body or selected parts of the body could be coated.

In an open environment, such as a beach or a park, a modified version of configuration illustrated in FIG. 7 could be used to rapidly coat an individual. It would even be possible to have a walk-through coating system. An atomized spray could be produced from multiple nozzles arranged in a single line (as shown in FIG. 7), in two single lines facing one another and about 36 to about 48 inches apart, or multiple lines of nozzles. The preferred configuration is multiple lines, with 4 lines being adequate. The atomized spray results in an area of intense atomized solution, which would coat an individual standing in that area. The residual spray would then be dissipated into the surrounding environment. A fan could be used to accelerate the removal of the residuals from the coating area.

Figure 8:
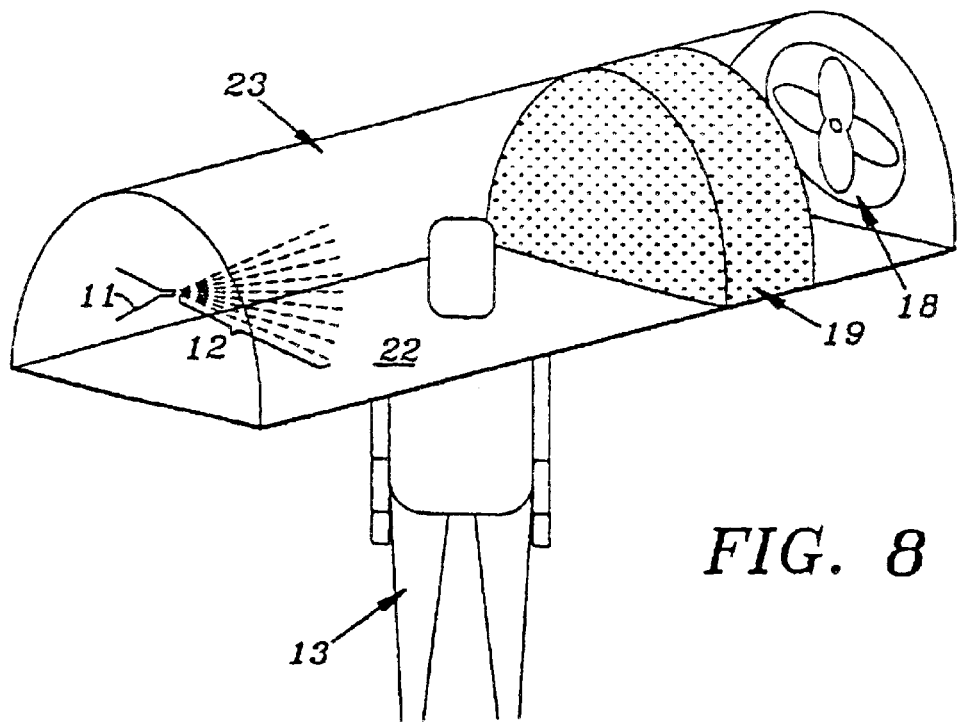
FIG. 8 is an illustration similar to FIG. 5 wherein the system of the present invention is adapted to the coating of a selected part of the human body.
Figure 9:
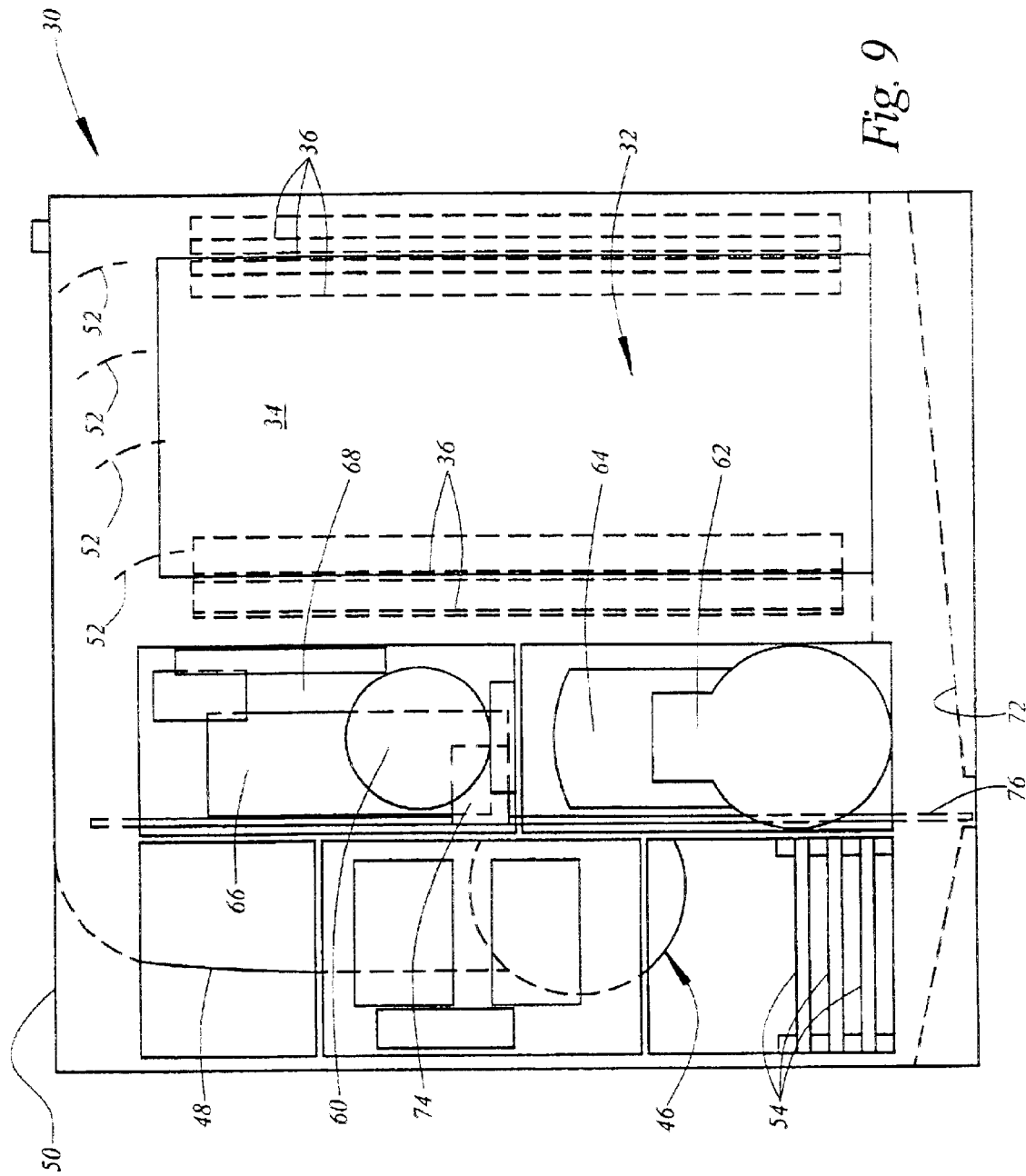
FIG. 9 is a front view of an apparatus useful in the practice of the invention.

FIG. 8 illustrates how the system of the present invention can be used to tan a selected part of the body. In this case, just the face is being tanned. In this figure the bottom panel of the apparatus 22 contains an opening through which one can insert his or her head. The top panel 23 is arched. The high-efficiency filter is 19. The fan and back panel is 18. Alternately, the setup as shown in FIGS. 2–7 could be used to tan only a select part of the body by protecting the area not desired to be tanned with appropriate barrier apparel or by screens between the atomized spray and the regions of the skin not to be coated. The barrier apparel could be any material impervious to the atomized coating composition. For example, materials appropriate for use with the aforementioned coating compositions include vinyl, polyurethane, and latex rubber. The screens can be sheets composed of any material impervious to the atomized artificial tanning compositions, including most metals or plastics. A preferred screening material is foam with an impervious aluminum foil backing. The foam is aligned with the backing away from the atomizing orifice. The foam is preferred because it absorbs much of the atomized spray, reducing back deflection.

FIGS. 9, 10, 11, and 12 illustrate an apparatus which may be utilized in the practice of the invention. The apparatus 30 comprises a unitary construction which includes both a coating chamber 32 adapted to receive a person to be coated with a includes both a coating chamber 32 adapted to receive a person to be coated with a predetermined substance and various components utilized to effect spraying of the predetermined substance onto the person situated within the coating chamber 32.

Figure 10:
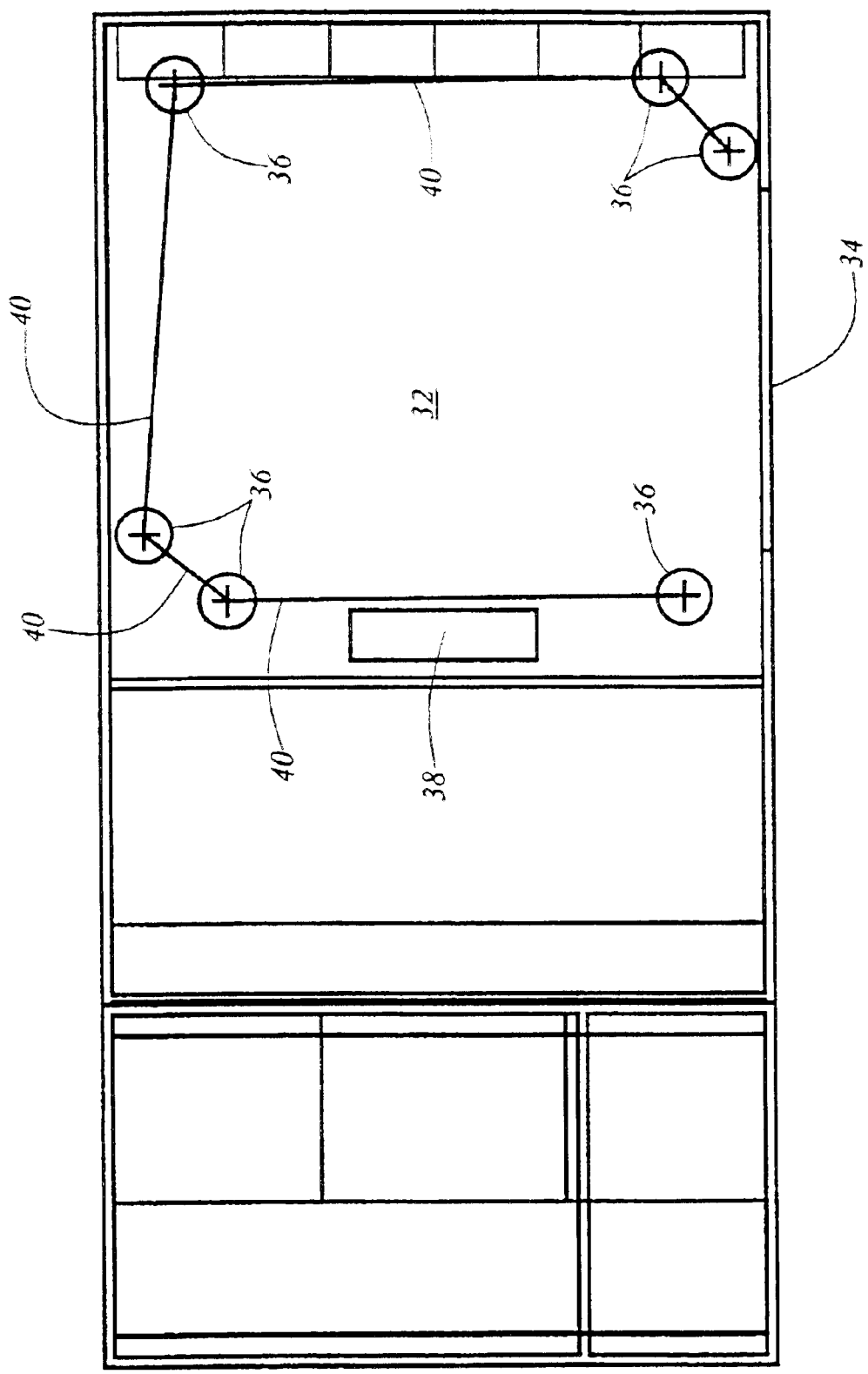
FIG. 10 is a top view of the apparatus of FIG. 9.

The coating chamber 32 includes a door 34 which affords ingress to and egress from the coating chamber. The coating chamber 32 is further provided with a plurality of spray columns 36. As is best shown in FIG. 10, the spray columns 36 are located at spaced apart points around the periphery of the chamber 32. Those skilled in the art will appreciate the fact that neither the number nor the precise location of the spray columns 36 is critical to the practice of the invention, and that other spray column arrangements may be utilized in the practice of the invention, if desired.

The spray columns 36 are preferably supported for pivotal movement through predetermined arcs under the action of a pneumatic cylinder 38. In this manner the predetermined material is discharged from the spray columns 36 in such a way as to assure uniform coating of the predetermined material on a person situated within the coating chamber 32. The pneumatic cylinder 38 is connected to the pivoting mechanism of each of the spray columns 36 through a plurality of links 40.

Referring again to FIG. 9, there is further included a blower 46 which directs a flow of air upwardly along an air guide 48 and then laterally along a top panel 50 into engagement with a plurality of baffles 52. The baffles 52 direct the air from the blower 46 downwardly through the coating chamber 32, whereby the flowing air effects drying of the sprayed material and aids in recovery of the sprayed material for reuse. From the coating chamber 32 the air is directed through a plurality of filters 54 and is returned to the blower 46.

The predetermined material which is to be coated onto a person situated within the coating chamber 32 is preferably provided in the form of a liquid which is received in a reservoir 60. The interior of the reservoir 60 is pressurized by compressed air which is received from an air compressor 62 through an air tank 64. Compressed air from the air compressor 62 in the tank 64 is also directed to an air tank 66 and to a manifold 68. The air tank 66 provides compressed air for operating the pneumatic cylinder (FIG. 10). The manifold 68 directs compressed air to the spray columns 36.

Ideally, all of the liquid from the reservoir 60 which is discharged from the spray columns 36 would be received on the body of the person within the coating chamber 32. In actual practice, it is not possible to obtain 100% efficiency in the coating procedure. Excess liquid which is discharged from the spray columns moves downwardly under the action of gravity onto a drain ramp 72. A drain pump 74 receives the excess liquid through a suction pipe 76 and delivers it to an appropriate drain.

Figure 11:
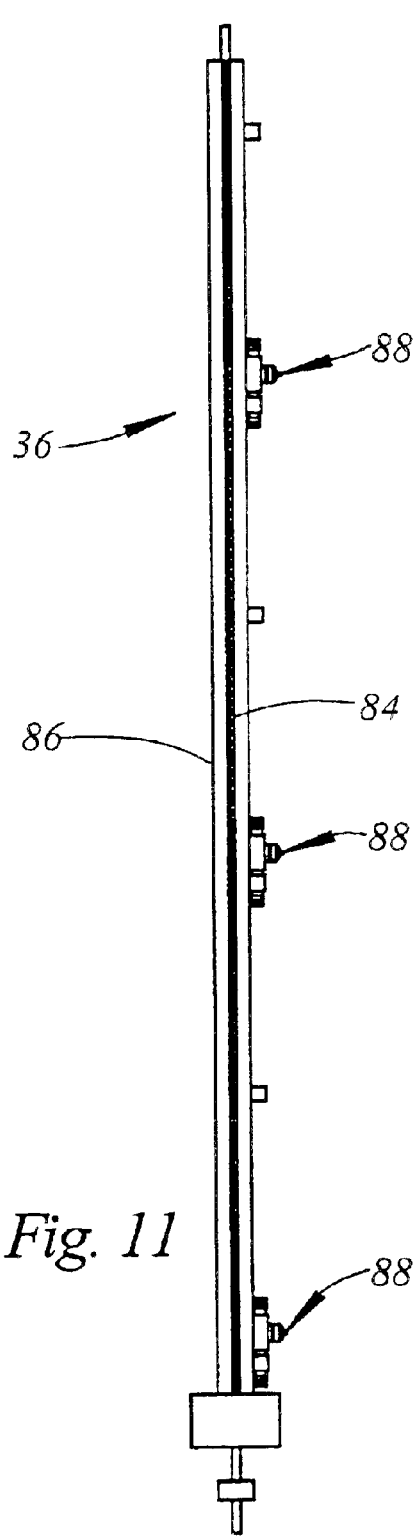
FIG. 11 is an illustration of one of the spray columns of the apparatus of FIG. 9.
Figure 12:
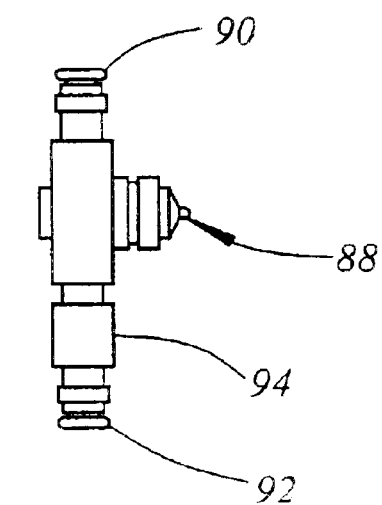
FIG. 12 is an enlarged view illustrating the nozzle assemblies utilized in the spray columns of the apparatus of FIG. 9.

Referring to FIGS. 11 and 12, each spray column 36 includes an inner tubular passageway 84 which receives liquid from the reservoir 60 under the action of compressed air supplied by the air compressor 62 through the tank 64 and an outer tubular passageway 86 which receives compressed air from the manifold 68. Each spray column 36 is provided with a plurality of nozzles 88. Each nozzle 88 receives compressed air from the outer tubular passageway 86 through a quick disconnect 90 and receives liquid from the inner tubular passageway 84 through a quick disconnect 92. A check valve 94 prevents reverse flow of liquid back through the quick disconnect 92.

Features Contributing Significantly to the Successful Operation of an Automated Coating System for the Human Body Incorporating the Invention Formula:

The following formula is a combination of water, dihydroxyacetone, bronzer, moisturizer, surfactant, and penetration enhancer. The formula is:

|  |  | Range | Preferred |
|---|---|---|---|
| water | base | 16%–65% | 41.7% |
| dihydroxyacetone | self-tanning | 3%–15% | 10.0% |
| bronzer* | cosmetic colorant | 0%–10% | 8.0% |
| ethoxy diglycol | penetration enhancer | 0%–10% | 5.0% |
| commercial moisturizer lotion** | film former, viscosity | 10%–25% | 15.0% |
| commercial bath product*** | surfactant | 0%–2% | 0.6% |
| citric acid | pH adjustment | 0.1%–1.0% | 0.2% |
| 10x aloe vera concentrate | moisturizer, tan enhancer | 1%–5% | 2.5% |
| isopropyl alcohol with methyl salicylate | solvent, penetration enhancer | 5%–25% | 15.0% |
| Trivosol ® | emulsifier | .5%–10% | 2.0% |

*By way of example, a suitable bronzer would be a combination of the following food dyes provided by Adams Extract Company, Austin, Texas: 4 parts red, 2 parts yellow, 1 part green, and 3 parts purple.
**By way of example, a suitable commercial moisturizer lotion includes Vaseline Intensive Care Lotion (Aloe Vera Triple Action Formula, Chesebrough-Ponds, Greenwich, CT).
***By way of example, a suitable commercial bath product includes Vaseline Intensive Care Foaming Creme Bath (Chesebrough-Ponds, Greenwich, CT).

Foot Shields:

The feet are one of the most difficult parts of the body to coat uniformly. This difficulty is due in large part to the irregular structure of feet. Also, the downward motion of the atomized mist, both by gravity and from air currents, tends to cause the mist to settle on the tops of the feet. Therefore, the feet are provided with shields to assure a more uniform coating of the feet. The shields may take the form of a large, bottomless shoe. The shields produce a silhouette effect from the top of the feet to the toes. Holes and openings are provided in the shields which are located 0.25 to 2 inches from the feet, allowing the mist to result in a silhouette effect rather than defined lines.

Air Shield to Deflect Air Away from the Feet:

To reduce the amount of mist settling on the feet, a plastic shield shaped like a figure eight is placed between the fleximat flooring the user stands on and the metal grating supporting the fleximat. Dimensions of the figure eight are two 18 inch diameter overlapping circles with a total width of 26 inches. The total width can vary from 18 inches to 36 inches, and the circle diameters can vary from 12 inches to 20 inches.

Toweling Buffing after Coating:

After coating it is advantageous to use a towel rub to buff over the entire body to yield a more uniform coating and to remove any areas of excess. The toweling yields a more cosmetically pleasing result and reduces transfer to clothing. It is preferred to towel using long, light strokes. A cotton bath towel 16 inches by 32 inches may be used. The towel could vary from a hand cloth (8"×8") to a large beach towel (18"×48"). Care must be taken not to rub so hard or too much as to rub off the coating (or tan). Basically, the weight of the preferred towel is adequate, without additional pressure.

Stance During Coating:

The stance used during the coating is important. After trial and evaluation of numerous methods, it has been discovered that the "ballerina stance" seems to work best. Key elements of the stance are:

hands over the head
    preferred 2 inches
    lower limit—hands touching head
    upper limit—arms extended fully up
hands parallel to the floor
    hands could be, but not recommended to be, perpendicular to floor in a praying stance, or facing downwardly
feet separated about 12 inches
feet separated about 12 inches
    to allow mist to coat inside of legs
    feet are flat on flooring
    use of feet shields as described above Hair Net:

Although the above-described self-tanning solution does not turn hair orange, it may accumulate on hair. To avoid this accumulation, the user can wear a hair net or bouffant. Preferred compositions for the hair net include a cloth or plastic mesh or a continuous plastic sheet.

Barrier Cream:

It has been discovered that the commercial barrier cream produced by GoJo blocks the tanning solution from the skin. During the coating process, this lotion can be used to prevent tanning of specific areas, such as the palms of the hands.

High Efficiency Filter:

The use of high efficiency filters to remove excess mist is important. Preferably, a Binks high-efficiency paint-pockets filter is used.

Recharging of Filter:

It has been discovered that the tanning solution trapped in the filter can be removed with a water rinse. The solution, which is water soluble, is flushed out using water that is back-washed (water applied to the top surface opposite of the surface facing the solution) or water, preferably under moderate (greater than 60 psi) pressure, that is hosed on the filtered surface.

Uniform Air Flow:

Uniformity of air flow is very important to assure that the mist continues to be applied uniformly over the body even after the pressurized spray stops. Air flow parameters are, in the downward motion:

| | |
|---|---|
| most preferred | 100 cfm |
| next preferred | 50 cfm to 200 cfm |
| next preferred | 25 cfm to 300 cfm |

Warming of Air:

Atomization of liquids as done here by the nozzles results in a significant reduction in liquid temperature (as much as 20° F.). To keep the temperature to a warm, pleasant experience, four halogen lamps (250 watts each) can be added to the system to provide both illumination and heat. A coating chamber temperature of 80° F. to 110° F. is preferred, with 90° F. to 100° F. being more preferred. Other heating devices include infrared lamps and electrical heating elements.

EXAMPLES

Example 1

A twenty year old female of type III skin tanned by this process. She first applied a heart shaped sticker on her right arm. She covered her hair with a nylon mesh hair net and applied barrier cream over the palms of her hands. She tanned in the coating chamber. The subject above was coated for 7 seconds. About 300 grams of solution was applied during such time. There was a subsequent 7 second period in which the mist was circulated in the booth. The residual mist was removed from the booth and the subject dried for about 45 seconds. The subject then removed any excess lotion with a towel. The final result was that the subject was 1 to 2 shades darker after tanning. This difference was especially apparent when comparing the area under the sticker with the area with no sticker. The initial color was mainly from the bronzer, and is a deep brown color. Color was much more intense the next day, when the color was at least two shades darker than before tanning. After the subject showered, the intensity was dropped to about 1 shade darker than prior to tanning. This color, which was mainly from the dihydroxyacetone, was golden-brown. The color persisted about 1 shade darker for 3–4 days, and noticeable color was present for 7 days.

Example 2

A forty-seven year old male with type II skin tanned by this process. He first applied a heart shaped sticker on his right arm. He covered his hair with a nylon mesh hair net and applied barrier cream over the palms of his hands and the bottoms of his feet. He tanned in the coating chamber. The subject above was coated for 7 seconds. About 300 grams of solution was applied during time. There was a subsequent 7 second period in which the mist was circulated in the booth. The residual mist was removed from the booth and the subject dried for about 45 seconds. The subject then removed any excess lotion with a towel. The final result was that the subject was about 1 shade darker after tanning. This difference was especially apparent when comparing the area under the sticker with the area with no sticker. The initial color was mainly from the with the area with no sticker. The initial color was mainly from the bronzer, and is a deep brown color. Color was much more intense the next day, when the color was one to two shades darker than before tanning. After the subject showered, the intensity was dropped to about 1 shade darker than prior to tanning. This color, which was mainly from the dihydroxyacetone, was golden-brown. The subject repeated the tanning process again later the second day. This time, the initial tan from the combination of previous tan and new bronzer was about 2 shades darker than before. Even after showering the next day, the tan was about two shades darker than prior to initially tanning. The color persisted about 2 shades darker for 3–4 days, and noticeable color was present for 10 days.

Example 3

A 24 year old female with type II skin tanned as described in examples 1 and 2 for five consecutive days. The results were a highly uniform, very dark tan. Her skin color was about 3 shades darker by the end of the week. The color was golden-brown. The color remained 2 to 3 shades darker for about 4 days, and some color (about 1 shade) was observed after 7 days.

Discoveries

Very Fast Drying:

Traditional sunless tanning products require 20 minutes or more to dry. The sunless tanning composition of the present invention drys within a minute after use.

Less Transfer to Clothing than Expected:

Traditional sunless tanning products do not contain bronzers because bronzers transfer to clothing and other fabrics. The present invention exhibits almost no such transfer.

Tan Hue Less Orange than Expected:

The combination of bronzers, tan enhancers, and a super application process produces a long lasting, golden-brown color.

Hair is not Turned Orange:

Self-tanning lotions have been reported to turn body hair orange. The formulation and application of the present invention do not cause the hair to turn orange. First, the formulation does not penetrate the hair, but rather beads up on it. Next, it is applied in a very thin coat. The net result is that the hair does not turn orange.

Produces a Very Uniform Tan:

The present invention facilitates the application of a thin, uniform film over the entire body. Consequently, the resulting coating and tan is far superior to manual application methods.

Bronzer tends to last Longer than Expected:

The bronzer provides immediate color and a method for observing the uniformity of the tan. The uniformity of the bronzer application is greatly enhanced because it is applied in a uniform, thin film and its substantivity is enhanced because of deeper penetration into skin with the presence of a penetration enhancer.

Use of Ethoxy Diglycol as a Penetration Enhancer makes the Tan last Longer and more Uniform:

With the use of ethoxy diglycol, the duration of uniform intense tan has increased from an average of about 2 days to an average of about 4 days, and some color persists for up to 14 days.

The foregoing improved self-tanning composition is advantageously utilized in conjunction with the method and apparatus of the present invention.

Plural Component Systems

As is well known by those skilled in the art, the vast majority of cosmetics are single component systems. Examples include traditional creams, lotions, or sprays.

Plural component systems are a rare exception. Although many of cosmetic products would perform better as plural component systems, the consumer market generally does not like or cannot deal with multiple component systems. Even professionals, such as beauticians, generally prefer single component systems.

Even medical or industrial products are generally single component. Again, the end users do not like dealing with multiple component systems.

In some cases, these objections are circumvented by unique delivery systems with which automatically mix the components. One example of such a system is the dual syringe delivery apparatus used with two part epoxy systems. Another example comprises spray devices for applying paints and coatings using plural nozzle heads.

Figure 13:
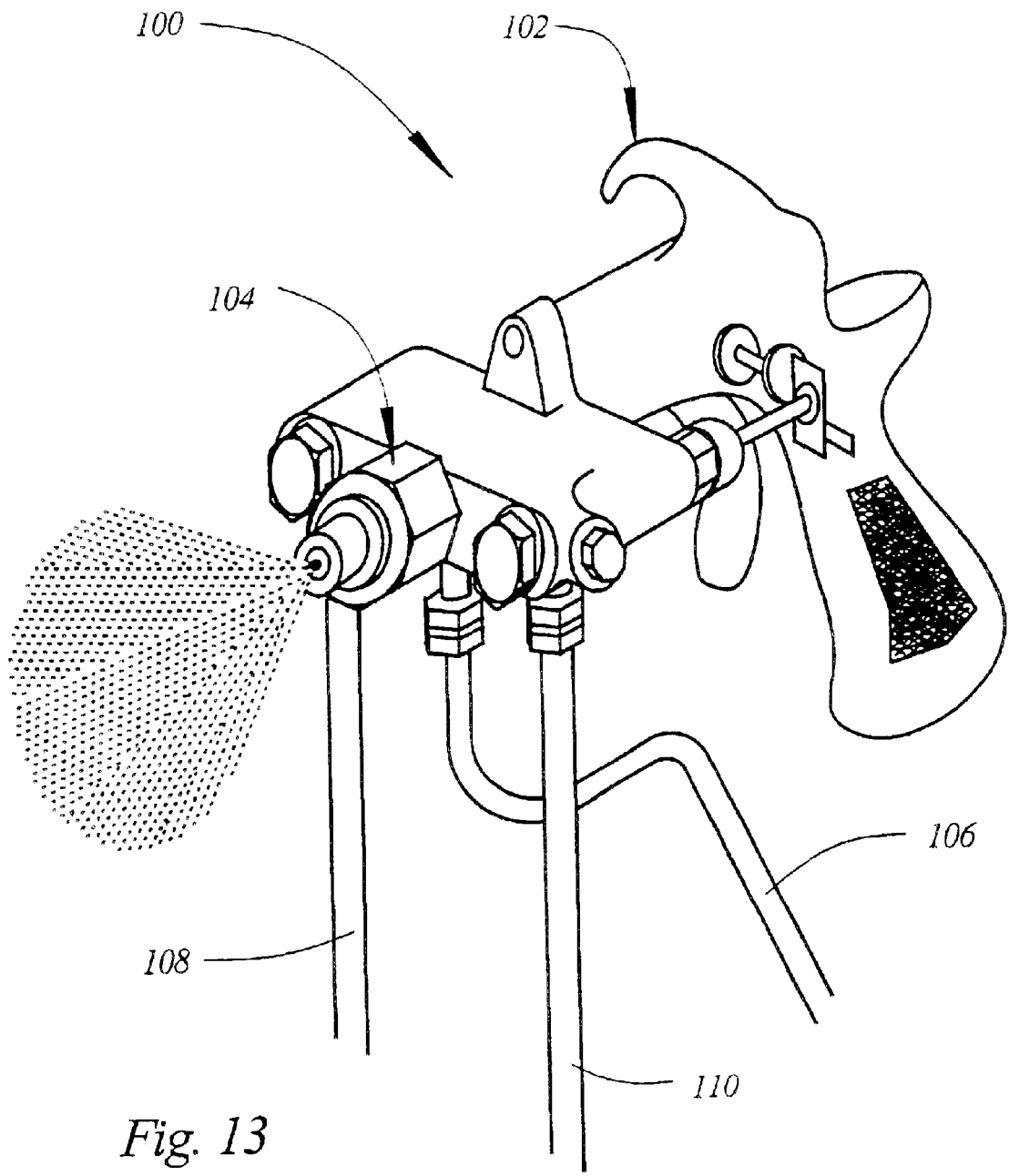
FIG. 13 is an illustration of a first type of prior art plural component spray discharge system.

Referring to FIG. 13, there is shown a plural component spraying system 100 of the type conventionally utilized in applying paints and coatings. The spray system 100 includes a spray gun 102 having a single nozzle 104. The spray gun 102 receives compressed air through a line 106. A first component of a composition to be applied is received through a line 108 and a second component of the composition as is received through a line 110. The two components are mixed in the nozzle 104 and discharged therefrom as a unitary composition.

Figure 14:
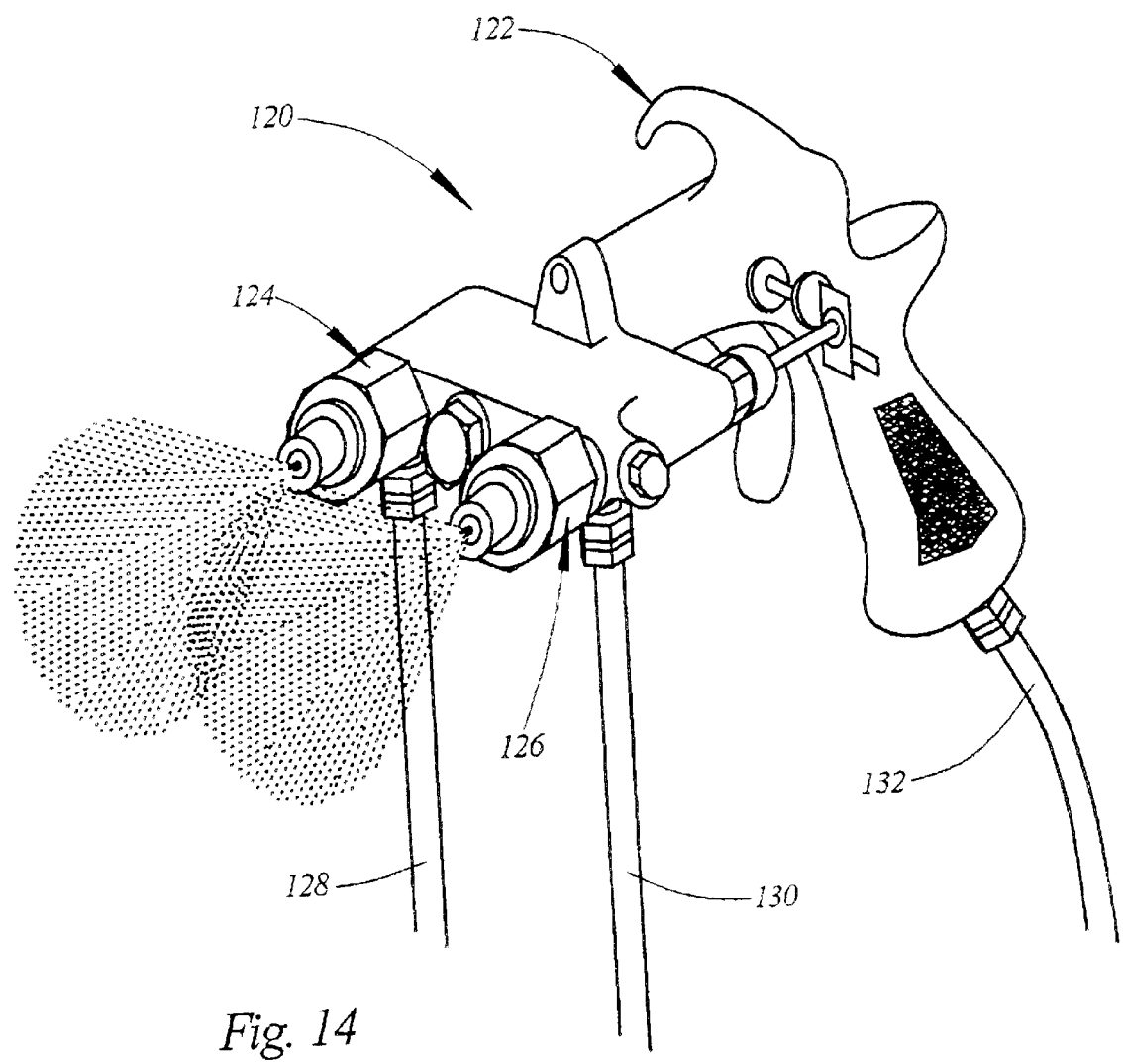
FIG. 14 is an illustration of a second type of prior art plural component spray discharge system.

Referring to FIG. 14, there is shown a plural component spraying system 120 of the type conventionally utilized in the application of paints and coatings. The plural component spraying system 120 includes a spray gun 122 having a dual discharge nozzles 124 and 126. A first component of a composition to be applied is received by the nozzle 124 through a line 128. A second component of the composition to be applied is received by the nozzle 126 through a line 130. Compressed air is directed to the spray gun 122 through a line 132.

In the operation of the plural component spraying system 120, the component parts of the composition to be applied are not mixed in the nozzles 124 and 126. Rather, the nozzles 124 and 126 each discharge a separate and distinct component of the ultimate composition to be applied. Mixing of the two components to form the ultimate composition occurs as the components which are discharged from the nozzles 124 and 126 simultaneously engage the surface to be coated.

Figure 15:
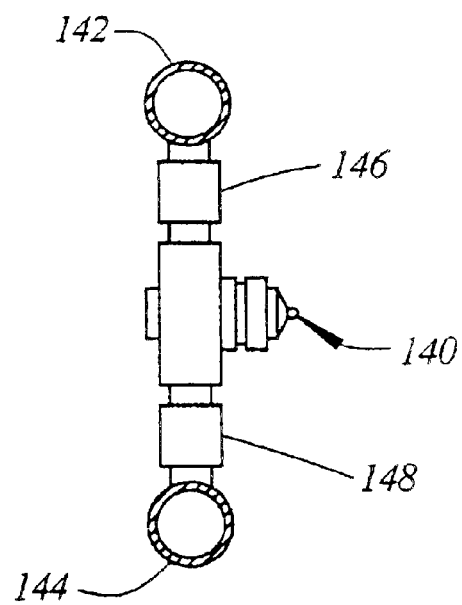
FIG. 15 is an illustration of a modification of the apparatus of FIGS. 9–12 to provide a plural component system.

FIG. 15 illustrates an adaptation of the apparatus illustrated in FIGS. 9, 10, 11, and 12 and described hereinabove in connection therewith whereby the apparatus is adapted for plural component spraying.

A nozzle 140 receives fluid from two passageways 142 and 144. Remotely operated valves 146 and 148 are utilized to control the flow of fluid from the passageways 142 and 144, respectively, to the nozzle 140.

The fluids received by the nozzle 140 from the passageways 142 and 144 through the remotely operated valves 146 and 148, respectively, may comprise the components of a plural component system to be applied, for example, to the human body. Alternatively, the passageways 142 and 144 may be utilized to supply entirely separate fluids which are applied sequentially. For example, a skin preconditioner could be supplied through the passageway 142 and discharged from the nozzle 140 for application to the skin of the person to be tanned, allowed to remain in contact with the skin of the person to be tanned for a predetermined period of time, and thereafter removed from the skin by towel rubbing prior to the application of a self-tanning composition which is received by the nozzle 140 through the passageway 144 and discharged by the nozzle onto the skin of the person to be tanned.

Those skilled in the art will appreciate the fact that the apparatus illustrated in FIG. 15 is not limited to receiving the discharging two fluids. Rather, multiple lines can be connected to the nozzle through multiple remotely operated or valve components thereby facilitating the application of a plurality of fluids either simultaneously or sequentially. The remotely operated valves are conventional in construction and operation and may operate responsive to electrical, electromagnetic, pneumatic, and/or hydraulic signals.

The plural component spraying systems shown in FIGS. 13, 14, and 15 can be used with a wide variety of nozzles, all of which are listed in U.S. Pat. No. 5,922,333 which is assigned to the assignee hereof. Included are traditional atomization nozzles and electrostatic nozzles.

The plural component spraying systems of FIGS. 13, 14, and 15 are advantageously used to apply self-tanning (a.k.a. sunless tanning) compositions. For example, a DHA/bronzer/moisturizer mixture may comprise a first component and a tan enhancing component, which normally would destabilize the DHA component, and may comprise the second component of a plural component self-tanning composition. Examples of the tan enhancing component include penetration enhancers and materials which effect the chemical binding of the DHA to skin components. By simultaneously or sequentially misting the two components, an enhanced tan is achieved without requiring the consumer to deal with a multi-component system.

In a second example, a plural component wrinkle treatment which includes solutions at different pHs, or which rapidly react with each other, is applied to the skin sequentially.

Yet another example comprises on-skin polymerization. This is used to spray apply a body barrier layer which is impervious to water, radiation, etc. In this example, the solutions which contain reactive ingredients come into contact only after being applied to the skin.

Still another example is the use of an activator and base. The two component hydrogen peroxide system which is disclosed in U.S. Pat. No. 6,117,118 is advantageously applied by a plural mist-on process illustrated in FIGS. 13, 14, and 15 and described hereinabove in conjunction therewith. The end effect is whole-body bleaching of a sunless tan.

Although preferred embodiments of the invention are illustrated in the drawings and described in the detailed description, it will be understood that the invention is not limited to the embodiments disclosed, but is capable of numerous modifications and rearrangements of parts and elements without departing from the spirit of the invention.

What is claimed is:

1. A plural component process for coating the human body comprising the steps of:
   providing a first component of a human body coating composition;
   providing a second component of the human body coating composition including an agent which would adversely effect the first component if mixed herewith;
   maintaining the first and second components of the human body coating composition separate from one another prior to application of the composition,
   simultaneously mixing the first and second components of the human body coating composition and spray-applying the human body coating composition onto a human body.

2. The process according to claim 1 wherein the mixing step is carried out by mixing the first and second components in a nozzle and immediately thereafter discharging the self-tanning composition from the nozzle onto the skin of a person.

3. The process according to claim 1 wherein the mixing step is carried out by simultaneously discharging the first and second components of the composition from separate nozzles onto the skin of a person so that the first and second components of the composition are mixed on the skin of the person.

4. A plural component self-tanning process comprising the steps of:
   providing a first component of a self-tanning composition which includes dihydroxyacetone;
   providing a second component of the self-tanning composition including a tan enhancing agent which would destabilize the dihydroxyacetone of the first component if mixed herewith;
   maintaining the first and second components of the self-tanning composition separate from one another prior to application of the self-tanning composition to effect self-tanning; and
   simultaneously mixing the first and second components of the self-tanning composition and spray-applying the self-tanning composition onto a human body.

5. The process according to claim 4 wherein the mixing step is carried out by mixing the first and second components of the self-tanning composition in a nozzle and immediately thereafter discharging the self-tanning composition from the nozzle onto the skin of a person to be tanned.

6. The process according to claim 4 wherein the mixing step is carried out by simultaneously discharging the first and second components of the self-tanning composition from separate nozzles onto the skin of a person to be tanned so that the first and second components of the self-tanning composition are mixed on the skin of the person to be tanned.

* * * * *

UNITED STATES PATENT AND TRADEMARK OFFICE
CERTIFICATE OF CORRECTION

PATENT NO. : 6,881,417 B1
APPLICATION NO. : 10/664572
DATED : April 19, 2005
INVENTOR(S) : Thomas J. Laughlin It is certified that error appears in the above-identified patent and that said Letters Patent is hereby corrected as shown below:

IN THE SPECIFICATION
Col. 1, line 12, replace "which is continuation-in-part" with
--which is a continuation-in-part--.

Col. 1, line 14, replace "application Ser. No. 09/294,689" with -- provisional application Ser. No. 60/154,948 filed September 21, 1999, abandoned, which is a continuation-in-part of application Ser. No. 09/294,689--.

Col. 1, line 36, replace "long standing" with --long-standing--.

Col. 2, line 19, replace "anti-microbial" with -- anti-microbials--.

Col. 2, lines 41-43, replace "retain more absorb or trap more formulation (e.g., the wrinkles in the elbows and knees and the dense tissue in the palms)" with -- retain more formulation. The result is that as the formulation is being spread manually, certain tissue absorb or trap more formulation (e.g., the winkles in the elbows and knees and the dense tissue in the palms)--.

Col. 4, line 24, replace "Dornicent" with --Domicent--.

Col. 6, lines 63-66, replace "Foaming Creme Bath (Chesebrough-Ponds, Greenwich, Conn.). The bronzer is a combination of FD&C dyes that yield a golden brown color. By way of example" with --By way of example--.

Col. 7, line 30, replace "at a pH 3.0" with --at a pH of 3.0--.

Col. 8, lines 35-37, replace "depends will result in a very dark tan. The exact amount of dihydroxyacetone required depends on the skin" with -- depends on the skin--.

Col. 8, line 60, replace "electrostatic" with -- •    electrostatic--.

Col. 10, lines 36-37, replace "guide the cubic feet per minute per square foot, the air movement is sufficient to guide the" with -- guide the--.

Col. 12, lines 20-21, replace "with a includes both a coating chamber 32 adapted to receive a person to be coated with a" with --with a --.

Col. 14, lines 33-34, replace "feet separated about 12 inches feet separated about 12 inches" with -- feet separated about 12 inches --.

UNITED STATES PATENT AND TRADEMARK OFFICE
CERTIFICATE OF CORRECTION

PATENT NO. : 6,881,417 B1
APPLICATION NO. : 10/664572
DATED : April 19, 2005
INVENTOR(S) : Thomas J. Laughlin It is certified that error appears in the above-identified patent and that said Letters Patent is hereby corrected as shown below:

IN THE SPECIFICATION (Continued)
Col. 15, lines 60-61, replace "mainly from the with the area with no sticker. The initial color was mainly from the" with -- mainly from the--.

Col. 16, line 66, replace "many of cosmetic" with -- many cosmetic--.

Col. 17, line 8, replace "systems with which" with -- systems which--.

Col. 17, line 20, replace "as is received" with -- is received--.

Col. 17, line 26, replace "having a dual" with --having dual--.

IN THE CLAIMS
Col. 18, Claim 1, line 55, replace "effect the first component" with -- affect the first component --.

Signed and Sealed this

Fifteenth Day of August, 2006

JON W. DUDAS
*Director of the United States Patent and Trademark Office*